US00PP23074P2

(12) United States Plant Patent
Dobres

(10) Patent No.: US PP23,074 P2
(45) Date of Patent: Sep. 25, 2012

(54) ***NEPETA* PLANT NAMED 'NOVANEPJUN'**

(50) Latin Name: *Nepeta hybrida*
Varietal Denomination: Novanepjun

(75) Inventor: Michael S. Dobres, Philadelphia, PA (US)

(73) Assignee: Novaflora Inc., West Grove, PA (US)

( * ) Notice: Subject to any disclaimer, the term of this patent is extended or adjusted under 35 U.S.C. 154(b) by 0 days.

(21) Appl. No.: 13/137,211

(22) Filed: Jul. 28, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — Buchanan Ingersoll & Rooney PC

(57) ABSTRACT

The present *Nepeta* plant was created by the gamma-ray mutagenesis of the 'Walker's Low' variety. A low mounding growth habit is displayed which is lower than that of the 'Walker's Low' variety. The foliage is medium green and provides a mint fragrance. Attractive generally upright purple-violet flowers are formed in abundance over an extended period of time. The plant can be grown to advantage as attractive ornamentation in parks, gardens, and residential settings.

1 Drawing Sheet

Botanical/commercial classification: *Nepeta hybrida*/Catmint Plant.

Varietal denomination: cv. Novanepjun.

SUMMARY OF THE INVENTION

*Nepeta* plants sometimes are identified by the use of Catmint common name.

The new variety of *Nepeta hybrida* of the present invention was derived from the *Nepeta*×*Faassenii* 'Walker's Low' variety (non-patented in the United States) of through the use of induced mutagenesis followed by selection. More specifically, on May 31, 2006 tissue cultured shoots of 'Walker's Low' variety were subjected to gamma irradiation to form a population of plants which included various mutations. The cultures were rooted during October 2006, were transferred to soil and were acclimatized during November 2006. The resulting plants next overwintered in a plant hut with minimal heat near West Grove, Pa., U.S.A. Thereafter the plants were cut back and were observed in detail for the possible presence of attractive novel phenotypes during the spring and summer of 2007. A single plant of the new variety of the present invention was selected in view of its novel phenotype. Had this plant not been selected and preserved it would have been lost to mankind.

It was found that the new *Nepeta* plant of the present invention exhibits the following combination of characteristics:

(a) displays a low mounting growth habit,
(b) forms in abundance over an extended period of time attractive generally upright flowers of purple-violet coloration,
(c) displays medium green foliage with a mint fragrance, and
(d) is particularly well-suited for growing as ornamentation.

The new variety well meets the needs of the horticultural industry. It can be grown to advantage as attractive low-growing ornamentation plant in parks, gardens, public areas, and residential settings. The attractive upwardly extending violet blossoms contrast nicely with the medium green foliage below.

The new variety of the present invention can be readily distinguished from previously available *Nepeta* varieties. For instance, the 'Walker's Low' variety, which was designated the 2007 Perennial Plant of the Year of the Perennial Plant Association, can be used as a comparative variety. When compared to the 'Walker's Low' variety, the new variety of the present invention forms smaller foliage and displays a more compact and lower growth habit. When mature plants of the new variety commonly assume a height of approximately 1½ feet and a width of approximately 2½ feet. This can be compared to a typical mature height of approximately 2½ feet and width of approximately 4 feet for the 'Walker's Low' variety. Also, when compared to the 'Blue Wonder' variety (non-patented in the United States), the 'Blue Wonder' variety typically displays a taller growth habit. When the new variety is compared to the 'Kit Kat' variety (non-patented in the United States), the 'Kit Kat' variety commonly is even lower growing and is later blooming.

Asexual reproduction of the new variety in a controlled environment by the rooting of terminal cuttings has been conducted near West Grove, Pa., U.S.A., beginning in 2007. It has been demonstrated that the combination of characteristics of the new variety are firmly fixed and are well retained in succeeding generations. Accordingly, the new variety can be asexually reproduced in a true-to-type manner.

The new cultivar has been named 'Novanepjun'.

BRIEF DESCRIPTION OF THE PHOTOGRAPH

The accompanying photograph was prepared during June and illustrates a typical container-grown flowering plant of the new variety. The plant had been reproduced by the rooting of a cutting, was approximately one year of age, and was being grown near West Grove, Pa., U.S.A. The typical low mounding growth habit with generally upright purple-violet blossoms is displayed.

DETAILED DESCRIPTION

The chart used in the identification of the colors described herein is The R.H.S. Colour Chart of The Royal Horticultural Society, London, England (1995 Edition or equivalent). In some instances, more common color terms may be provided and are to be accorded their usual dictionary significance. The plants had been asexually reproduced by the rooting of cuttings, were approximately one year of age, and were observed while growing in containers during June near West Grove, Pa., U.S.A.

Botanical classification: Mutagenized selection of *Nepata*× *faassenii* 'Walker's Low'.

Cultivar: Novanepjun.

Common name: CATMINT.

Plant:

*Form*.—Herbaceous perennial.

*Habit*.—Low and mounding with generally upright flowers above the foliage.

*Height*.—Approximately 1½ feet on average including the inflorescence.

*Width*.—Approximately 2½ feet on average.

Branches:

*Number*.—Commonly approximately 42 per plant.

*Length*.—Commonly approximately 12 inches on average.

*Diameter*.—Commonly approximately 2 mm on average.

*Internode length*.—Commonly approximately 3 cm on average.

*Texture*.—Rugose.

*Color*.—Near Yellow-Green Group 146B.

Foliage:

*Arrangement*.—Opposite, simple.

*Length*.—Commonly approximately 3.5 cm on average.

*Width*.—Commonly approximately 2 cm on average.

*Shape*.—Deltoid-cordate.

*Apex*.—Acute.

*Base*.—Cordate to truncate.

*Margin*.—Crenate.

*Texture*.—Rugose on both surfaces.

*Fragrance*.—Aromatic, mint fragrance.

*Color*.—Commonly near Green Group 143C on the upper surface, and Green Group 138B on the under surface.

*Venation pattern*.—Substantially longitudinal.

*Petioles*.—Commonly approximately 3 mm in length on average and approximately 2 mm in diameter on average, with short pubescence, near Green Group 143C on the upper surface, and near Green Group 138B on the under surface.

*Venation color*.—Upper surface: near Green Group 137A. Under surface: near Green Group 138B.

Inflorescence:

*Flowering season*.—Commonly May to September near West Grove, Pa., U.S.A.

*Lastingness*.—Individual blooms commonly last approximately one week on the plant.

*Arrangement*.—Elongate racemes with axially disposed cymes subtended by leafy bracts.

*Buds*.—Shape: generally ovoid. Length: approximately 5 mm on average. Diameter: approximately 2 to 3 mm on average. Color: near Violet Group 83C.

*Pedicels*.—Arrangement: commonly approximately 45 degrees to rachis. Length: approximately 2 mm on average. Diameter: approximately 1 mm on average. Texture: commonly bear short pubescence. Color: Violet Group 83D.

*Flowers*.—Shape: zygomorphic, bilabiate. Petal arrangement: five-petaled, with two fused petals on the upper lip, three fused petals on the lower lip, with all five petals being fused at the base to form a funnel-shaped structure. Number per cyme: commonly approximately 96 on average. Diameter (flower face): commonly approximately 0.7 cm on average. Depth: approximately 1.3 cm on average. Funnel: the corolla commonly is approximately 9 mm in length on average, approximately 1 mm in diameter on average at the opening, bears short pubescence on the outside, Violet Group 87D on the inside (throat), and Violet Group 87C on the outside. Color: face/margin on the upper surface commonly is Violet Group 87D, and on the under surface commonly is Violet Group 87C. Petal apex: rounded for upper and lower lips. Petal base: all petals fused. Petal margin: entire for all petals. Petal texture: glabrous. Petal shape on upper lip: bi-lobed comprised of two fused petals each having a rounded apex with an entire margin. Petal shape on lower lip: comprised of three fused petals that are crenate in appearance, each having a rounded apex and an entire margin. Petal length: commonly approximately 0.3 cm on average for upper lip, and approximately 0.6 cm on average for the lower lip. Petal width: commonly approximately 0.4 cm on average for the upper lip, and approximately 0.6 cm on average for the lower lip. Bract number: two per verticillasters. Bract length: approximately 8 mm on average. Bract width: approximately 3 mm on average. Bract shape: lanceolate. Bract apex: acute. Bract base: truncate. Margin: entire. Texture: rugose on both surfaces. Color: near Green Group 143C on the upper surface, and near Green Group 138B on the under surface. Sepal number: five fused sepals form a calyx tube. Sepal length: commonly approximately 0.6 cm on average. Sepal width: commonly approximately 0.2 cm on average. Sepal shape: somewhat tubular. Sepal apex: acute. Sepal base: fused. Sepal margin: entire. Sepal texture: with short pubescence on both surfaces. Sepal color: when fully open the upper and lower surfaces commonly are Yellow-Green Group 145A overlaid with Violet Group 83D. Peduncle length: commonly approximately 7 cm on average. Peduncle diameter: commonly approximately 1 cm on average. Peduncle aspect: substantially erect. Peduncle color near Green Group 143C. Stamen number: four. Filament length: approximately 0.4 cm on average. Filament diameter approximately 0.1 to 0.2 mm on average. Filament color. Violet Group 84D. Anther shape: bi-lobed. Anther length: approximately 0.8 mm on average. Anther width: approximately 0.2 mm on average. Pollen: none observed. Pistil number: one. Stigma shape: bifid. Stigma length: approximately 1.5 mm on average. Stigma color: Purple Group 77A. Style disposition: substantially erect. Style length: approximately 5 mm on average. Style diameter: approximately 0.2 mm on average. Style color: Purple Group 75A.

Ovary color: near Yellow-Green Group 144B. Fragrance: none detected. Fruit and seed set: none observed.

Disease resistance: During observations to date believed to be typical of the genus.

Insect resistance: During observations to date believed to be typical of the genus.

The 'Novanepjun' plant has not been observed under all possible environmental conditions to date. Accordingly, it is possible that the phenotype may vary somewhat with variations in the environment, such as temperature, light, day length, contact with pesticides, etc.

I claim:

1. A new and distinct *Nepeta* plant, having the following combination of characteristics:

(a) displays a low mounding growth habit, (b) forms in abundance over an extended period of time attractive generally upright flowers of purple-violet coloration, (c) displays medium green foliage with a mint fragrance, and (d) is particularly well-suited for growing as ornamentation;

substantially as illustrated and described.

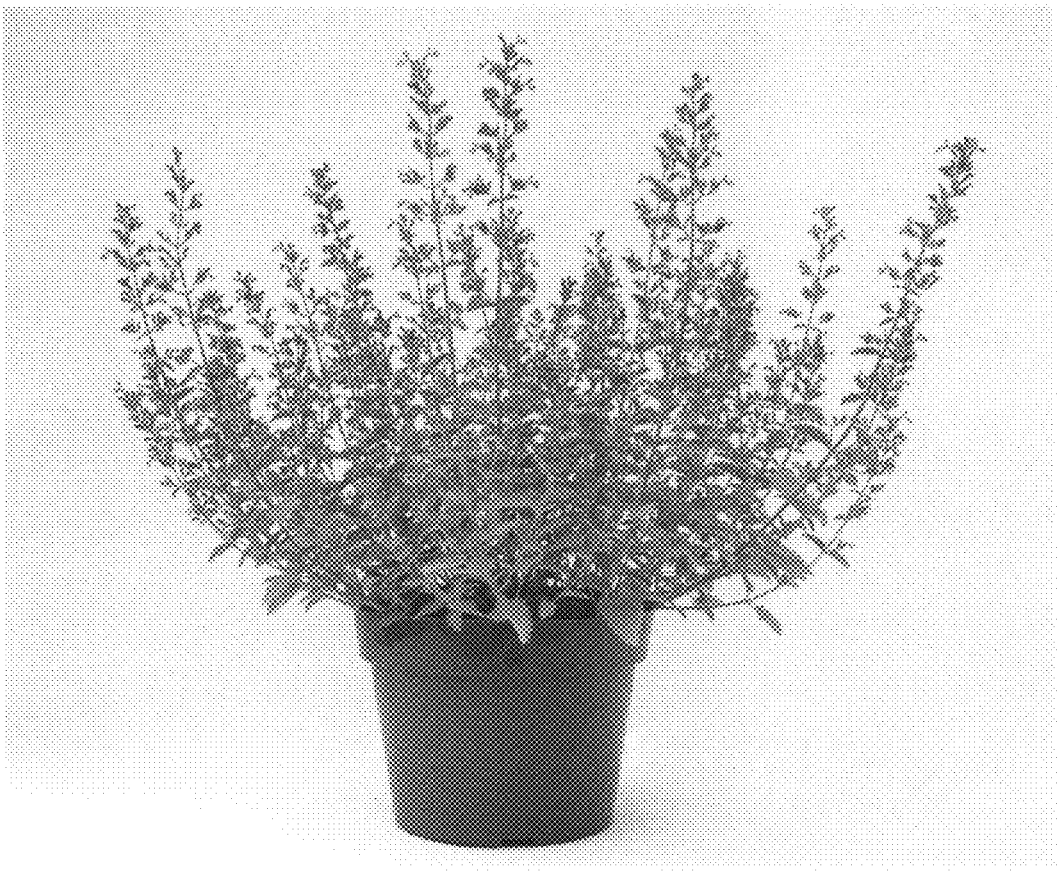

* * * * *